United States Patent
Peters et al.

(10) Patent No.: US 10,035,755 B2
(45) Date of Patent: Jul. 31, 2018

(54) METHOD FOR PRODUCING HALOGEN-N,N-DIMETHYLBENZYLAMINES

(71) Applicant: LANXESS Deutschland GmbH, Cologne (DE)

(72) Inventors: Lars Peters, Leverkusen (DE); Andreas Schulze Tilling, Leichlingen (DE); Wolfgang Stirner, Bergisch Gladbach (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/772,127

(22) PCT Filed: Mar. 4, 2014

(86) PCT No.: PCT/EP2014/054108
§ 371 (c)(1),
(2) Date: Sep. 2, 2015

(87) PCT Pub. No.: WO2014/135508
PCT Pub. Date: Sep. 12, 2014

(65) Prior Publication Data
US 2016/0002146 A1 Jan. 7, 2016

(30) Foreign Application Priority Data

Mar. 6, 2013 (EP) .................... 13158020
Sep. 10, 2013 (EP) .................... 13183790

(51) Int. Cl.
*C07C 209/28* (2006.01)
*C07C 209/26* (2006.01)

(52) U.S. Cl.
CPC .......... *C07C 209/28* (2013.01); *C07C 209/26* (2013.01)

(58) Field of Classification Search
None
See application file for complete search history.

(56) References Cited

U.S. PATENT DOCUMENTS

| | | | |
|---|---|---|---|
| 5,011,996 A | 4/1991 | Kiel et al. | |
| 5,071,924 A | 12/1991 | Koch et al. | |
| 6,429,335 B1 * | 8/2002 | Kiel | C07C 209/26 564/384 |
| 6,462,236 B2 * | 10/2002 | Liang | C07C 209/26 564/336 |
| 2002/0082455 A1 | 6/2002 | Liang et al. | |
| 2011/0065681 A1 | 3/2011 | Wei et al. | |

OTHER PUBLICATIONS

Bhattacharyya, S. "A high throughput synthesis of N, N-dimethyl-tertiary amines", Synthetic Communications, 30(11), (2000), pp. 2001-2008.
International Search Report from co-pending Application PCT/EP2014/054108 dated May 6, 2014, 3 pages.

* cited by examiner

Primary Examiner — Clinton A Brooks

(57) ABSTRACT

The invention relates to a method for producing halogen-N,N-dimethylbenzylamines wherein halogen=chlorine or bromine, preferably chloro-N,N-dimethylbenzylamines, preferably ortho-chloro-N,N-dimethylbenzylamine (o-Cl-DMBA), by reductive amination in the absence of sulfur.

10 Claims, No Drawings

METHOD FOR PRODUCING HALOGEN-N,N-DIMETHYLBENZYLAMINES

The invention relates to a method for producing halogen-N,N-dimethyibenzylamines wherein halogen chlorine or bromine, preferably chloro-N,N-dimethylbenzylamine (Cl-DMBA) by reductive amination. The method according to the invention has the advantage here that it can be carried out in the absence of sulfur.

BACKGROUND INFORMATION

It is known that firstly a hemiaminal is formed from an aldehyde and a secondary amine (amination) and this can also further react with another molecule of the amine to give the aminal with the elimination of water.

All of the specified reaction products (hemiaminal and aminal) can be hydrogenated catalytically to the corresponding amines. This reduction is described for example in Houben-Weyl, Methoden der Organischen Chemie [Methods of organic chemistry], 4th edition, volume IV/1c (1980), p. 127/128, 239/240 and 438. Such catalytic hydrogenations are also supposed to be possible while retaining halogen. However, this result is limited to the use of palladium catalysts, and it is further indicated that it is advantageous to work with deactivated catalyst and at relatively low temperatures (Houben-Weyl, Methoden der Organischen Chemie [Methods of organic chemistry], 4th edition, volume IV/1c (1980), page 240). Halogen is also supposed to be retained when using other catalysts such as platinum or Raney nickel. However, the specific hydrogenations indicated in the cited passages do not constitute a systematic investigation (Houben-Weyl, Methoden der Organischen Chemie [Methods of organic chemistry], 4th edition, volume IV/1c (1980), page 436, paragraph 3) and at times exhibit extremely moderate yields, as in the case of p-chlorobenzyl methyl ketone, which can be converted to the appertaining amine only in 10% of the theoretical yield (Houben-Weyl, Methoden der Organischen Chemie [Methods of organic chemistry], 4th edition, volume IV/1c (1980), page 436, at the bottom), Particularly when producing strongly basic amines, by-products have to be expected (Houben-Weyl, Methoden der Organischen Chemie [Methods of organic chemistry], 4th edition, volume IV/1c (1980), page 240, paragraph 2).

EP-A-0 355 351 discloses the catalytic hydrogenation in the presence of sulfur in the form of organic sulfur compounds. However, sulfur compounds have the disadvantage that they have to be precisely metered in since they poison the catalyst in the event of an incorrect dose or overdose. Moreover, sulfur compounds have negative effects on the end product, particularly chloro-N,N-dimethylbenzylamine, meaning that they have to be separated off, which entails expense.

Furthermore, WO 20091110985 discloses producing halogen-N,N-dimethylbenzylamines wherein halogen bromine from sodium cyanoborohydride. However, this method has the disadvantages that cyanides are released since sodium cyanoborohydride has to be used in a high excess and, as a consequence of this, a high salt content is produced which has to be disposed of in a costly manner. These methods are not suitable on an industrial scale on account of the high salt content and the toxicity of the sodium cyanoborohydride.

Alternative methods, as described in EPA 0355315, provide the addition of solid co-catalysts which have the disadvantage that they can bleed, meaning that they are found as undesired by-product in the end product.

In the methods according to the prior art, either expensive precious metal catalysts are used, only low yields are achieved, or the added additives have to be separated off in an expensive manner, which often renders these methods uneconomical.

Against the background of the aforementioned prior art, the object was therefore to provide a particularly economical method which permits the production of halogen-N,N-dimethylbenzylamines wherein halogen Cl or Br, preferably chloro-N,N-dimethylbenzylamine, particularly preferably ortho-chloro-N,N-dimethylbenzylamine (o-Cl-DMBA), in high yields and in the absence of sulfur and sulfur-containing compounds or other catalyst poisons or additives which reduce the catalyst activity.

SUMMARY OF THE INVENTION

Surprisingly, it has been found that the disadvantages of the prior art can be avoided and halogen-N,N-dimethylbenzylamines wherein halogen Cl or Br, preferably Cl, can be produced in a high yield and in the absence of sulfur if, during the reductive amination, a certain molar ratio of halogenbenzaldehyde wherein halogen=Cl or Br to dimethylamine is observed.

DESCRIPTION OF THE INVENTION

The present invention therefore provides a method for producing halogen-N,N-dimethylbenzylamines wherein halogen Cl or Br, preferably o-, m- or p-chloro-N,N-dimethylbenzylamine, very particularly preferably o-chloro-N,N-dimethylbenzylamine, by reductive amination of halogenbenzaldehyde wherein halogen=chlorine or bromine with dimethylamine in the presence of a catalyst selected from the group palladium, platinum, ruthenium, nickel or cobalt or Ni-containing and/or Co-containing catalysts, preferably of an Ni-containing and/or Co-containing catalyst, wherein the reaction is carried out in the presence of acids, preferably formic acid, acetic acid or propionic acid, particularly preferably acetic acid, and wherein the molar ratio of halogenbenzaldehyde wherein halogen=Cl, Br to dimethylamine is 1:>1.5. Halogen here can be in o- (=ortho), m- (=meta) or p- (=para)-position, preferably in o-position.

Particular preference is given to a molar ratio of halogenbenzaldehyde to dimethylamine of 1:1.51-10, very particularly preferably of 1:2-5.

The halogenbenzaldehydes used are standard commercial compounds which are commercially available e.g. under the names 2-chlorobenzaldehyde from Merck Millipore GmbH or 3-chloro- or 4-chlorobenzaldehyde from Alfa Aesar GmbH & Co KG.

The dimethylamine used is a standard commercial compound which is commercially available under the names dimethylamine anhydrous 2.8 (99.8% strength) from GHC Gerling, Holz and Co. Handels GmbH.

The catalysts used according to the invention are palladium, platinum, ruthenium and also nickel and/or cobalt. Preference is given to Ni and/or Co catalysts produced by leaching out from Ni or Co alloys, Ni or Co on supports, in the form of skeletal catalysts, elemental Ni(Co) sponge, as Ni oxide, Co oxide, Raney nickel, Raney cobalt. Supports are, for example, $SiO_2$, $Al_2O_3$, pumice, carbon and other supports known to the person skilled in the art. Particular preference in this connection is given to catalysts, such as Ni or Co catalysts, produced by leaching out from Ni or Co alloys which used as constituent of the alloy inter alia alloy of nickel, cobalt, nickel-iron, nickel-cobalt or nickel-iron-cobalt in anhydrous or else water-moist or solvent-moist form. The Ni- and Co-containing catalysts can also be used together.

In a preferred embodiment of the invention, the method is carried out in the absence of cocatalysts selected from the group of metal oxides or metal mixed oxides, zeolites, metal or ammonium salts of mineral acids or organic acids, acidic ion exchangers or mixtures thereof.

Skeletal catalysts are understood as meaning those catalysts which are produced by leaching out with strong bases, preferably with concentrated sodium hydroxide solution, The porous structure that is formed as a result is also termed skeletal structure.

The catalyst is used here preferably in an amount of 0.1-25% by weight, preferably 1.5-12.5% by weight, based on the substrate to be hydrogenated.

In a particularly preferred manner, Ni-containing skeletal catalysts are used. The catalysts are standard commercial catalysts, as are produced e.g. by H.C. Starck GmbH.

The reaction can take place here in the presence or else also in the absence of solvents, with the absence of solvents being preferred.

Solvents that can be used are alcohols, preferably methanol, ethanol, isopropanol, butanol, aliphatic or aromatic hydrocarbons, preferably toluene, xylene, cyclohexane, isooctane and the like, ethers, such as tetrahydrofuran, dioxane or methyl tert-butyl ester, esters such as ethyl acetate and finally the reaction product itself provided it is liquid at the reaction temperature. A content of water (e.g. up to 20% by weight) is not a problem, particularly if the reaction medium is miscible with water.

The hydrogenation is preferably carried out at 30-250° C., preferably at 50-150° C., and at an $H_2$ pressure of 5-250 bar, preferably 10-220 bar.

The hydrogen used for the hydrogenation is preferably commercially available hydrogen.

In general, the method according to the invention is carried out by initially introducing dimethylamine and the halogenbenzaldehyde, the add, optionally the solvent and the catalyst, in an hydrogenation autoclave and, after dosing the reactor, admixing the air with inert gas, preferably argon and nitrogen, and then displacing the inert gas with hydrogen, Hydrogen is then used to establish the desired pressure. In a preferred embodiment of the invention, stirring is carried out afterward until the pressure of the subsequently introduced hydrogen remains constant. When the reaction is complete (hydrogen absorption), the reaction vessel is firstly decompressed, preferably coded to room temperature and emptied; the catalyst is filtered off and can be reused without preparation.

The method can be carried out either discontinuously or continuously, preferably in a fixed-bed reactor.

In a preferred embodiment, acetic acid is added as acid during the reductive amination. This is standard commercial acetic acid, in a concentration range from 0.1 to 10%, which is available e.g. from Merck Millipore. h a preferred embodiment of the invention, the content of acetic acid is preferably 0.5-5% by weight, particularly preferably 0.5-4% by weight.

In a further preferred embodiment of the invention, the method is carried out in the absence of sulfur.

In the context of the invention, all of the radical definitions, parameters and explanations specified above or listed below, in general terms or in preferred ranges, can be combined with one another, thus also between the respective ranges and preferred ranges in any desired manner.

The examples below serve to illustrate the invention without having a limiting effect.

EXAMPLES 150 g (1.06 mol) of o-chlorobenzaldehyde, 3 g (0.05 mol) of glacial acetic acid and 6 g of nickel catalyst (a catalyst from HC Starck GmbH) were introduced together in a 0.7 L VA autoclave. The autoclave was closed, and at room temperature 213.6 g (4.74 mol) of dimethylamine were injected. Hydrogen was then used to establish a pressure of 50 bar and the system was heated to 100° C. After reaching the target temperature, the internal pressure was increased to 200 bar with hydrogen and maintained. As soon as the pressure of the subsequently supplied hydrogen remained constant, the mixture was then stirred for 30 min at 100° C. When the hydrogen absorption was complete and after cooling to room temperature, the reaction mixture was discharged (294.5 g of crude product, without work-up) and solid fractions of catalyst and by-products were separated off by filtration. The product is analyzed by gas chromatography and the yield is determined on the basis of this.

| Experiment | Solvent | I/C | Parameters | Molar ratio o-Cl-benzaldehyde:dimethylamine | Yield of o-Cl—N,N-dimethylbenzylamine |
| --- | --- | --- | --- | --- | --- |
| 1 | without | C | 50 bar, 150° C., | 1:1.5 | 0.7 |
| 2 | without | I | 50 bar, 150° C. | 1:4.5 | 55.5 |
| 3 | without | C | 150 bar, 150° C. | 1:1.5 | 50.7 |
| 4 | without | I | 150 bar, 150° C. | 1:4.5 | 73.3 |
| 5 | without | C | 50 bar, 90° C. | 1:1.5 | 78.1 |
| 6 | without | I | 50 bar, 90° C. | 1:4.5 | 81.9 |
| 7 | without | C | 150 bar, 90° C. | 1:1.5 | 81.1 |
| 8 | without | I | 150 bar, 90° C. | 1:4.5 | 90.6 |
| 9 | without | I | 100 bar, 120° C. | 1:3 | 85.5 |

C = comparison,
I = according to the invention

It is clearly evident from the examples that significantly better yields are attained at a molar ratio of o-chlorobenzaldehyde to dimethylamine of 1:>1.5.

What is claimed is:

1. A method for producing halogen-N,N-dimethylbenzylamines, the method comprising reductive amination of halogenbenzaidehyde with dimethyiamine in the presence of:
   hydrogen;
   an acid selected from the group consisting of formic acid, acetic acid, and propionic acid; and
   at least one catalyst selected from the group consisting of palladium, platinum, ruthenium, nickel, cobalt, nickel-containing catalyst and cobalt-containing catalyst,
   wherein the reductive amination is conducted:
   at a hydrogen pressure of 5 to 250 bar,
   at a temperature of 30-250° C.,
   with a molar ratio of the halogenbenzaidehyde to dimethylamine of 1:2-5, and
   without the addition of sulfur or further cocatalysts selected from the group consisting of metal oxides or metal mixed oxides, zeolites, metal salts of mineral acids, ammonium salts of mineral acids, metal salts of organic acids, ammonium salts of oroanic acids, acidic ion exchangers, and mixtures thereof.

2. The method as claimed in claim 1, wherein:
the halogen is chlorine or bromine; and
the reductive amination is done at a temperature of 50 to 150° C. at a hydrogen pressure of 10 to 220 bar.

3. The method as claimed in claim 1, wherein the catalysts are nickel (Ni) catalysts or cobalt (Co) catalysts produced by leaching out from Ni or Co alloys, Ni or Co on supports selected from the group $SiO_2$, $Al_2O_3$, pumice, carbon in the form of skeletal catalysts, elemental Ni(Co) sponge, as Ni oxide, Co oxide, Raney nickel, Raney cobalt.

4. The method as claimed in claim 1, wherein:
an amount of catalyst used in the reductive amination is 0.1-25% by weight based on the substrate to be hydrogenated; and
an amount of the acid used in the reductive amination is 0.1-10% by weight.

5. The method as claimed in claim 1, wherein the reductive amination is conducted without solvents.

6. The method as claimed in claim 1, further comprising conducting the reductive amination in the presence of at least one solvent selected from the group consisting of methanol, ethanol, isopropanol, butanol, toluene, xylene, cyclohexane, isooctane, tetrahydrofuran, dioxane, methyl tert-butyl ester and ethyl acetate.

7. The method as claimed in claim 1, wherein the molar ratio of the halogenbenzaldehyde to dimethyiamine is 1:1.51-10, and the method comprises conducting the reductive amination at a temperature of 50-150° C., and at an $H_2$ pressure of 10-220 bar.

8. The method as claimed in claim 1, wherein:
an amount of catalyst used in the reductive amination is 1.5-12.5% by weight based on the substrate to be hydrogenated; and
an amount of the add used in the reductive amination is 0.5-5% by weight.

9. The method as claimed in claim 1, wherein the acid is acetic acid.

10. The method as claimed in claim 1, wherein:
the halogen is chlorine, and the halogenbenzaldehyde is o-chlorobenzaldehyde;
the reductive amination is conducted at a temperature of 50-150° C., and at an $H_2$ pressure of 10-220 bar;
the at least one catalyst is a Ni or Co catalyst produced by leaching out from Ni or Co alloys, Ni or Co on supports selected from the group $SiO_2$, $Al_2O_3$, pumice, carbon in the form of skeletal catalysts, elemental Ni(Co) sponge, as Ni oxide, Co oxide, Raney nickel, Raney cobalt, and an amount of catalyst used in the reductive amination is 1.5-12.5% by weight based on the substrate to be hydrogenated; and
the acid is acetic acid, and an amount of the add used in the reductive amination is 0.5-4% by weight.

* * * * *